United States Patent [19]
Dineley et al.

[11] Patent Number: 5,209,411
[45] Date of Patent: May 11, 1993

[54] DECONTAMINATION OF MEDICAL WASTE

[75] Inventors: Christopher P. Dineley, Toronto, Canada; Robert A. Kolstad, Mesquite, Tex.

[73] Assignee: Cox Sterile Products, Inc., Dallas, Tex.

[21] Appl. No.: 808,978

[22] Filed: Dec. 17, 1992

Related U.S. Application Data

[63] Continuation of Ser. No. 589,185, Sep. 27, 1990, abandoned.

[51] Int. Cl.⁵ .............................................. B02C 23/00
[52] U.S. Cl. ...................................... 241/17; 241/23; 241/606
[58] Field of Search .................. 241/101.8, 99, 23, 65, 241/DIG. 38, 17, 23, 606

[56] References Cited

U.S. PATENT DOCUMENTS

| 4,185,973 | 1/1980 | Tester | 241/DIG. 38 X |
| 4,269,364 | 5/1981 | Moriconi et al. | 241/99 X |
| 4,705,222 | 11/1987 | Shohet | 241/101 B X |
| 4,860,958 | 8/1989 | Yerman | 241/99 X |
| 4,860,960 | 8/1989 | Schwartz | 241/101 B X |
| 5,054,696 | 10/1991 | Menner et al. | 241/606 X |

FOREIGN PATENT DOCUMENTS

| 54823 | 6/1982 | European Pat. Off. | 241/DIG. 38 |
| 1502093 | 8/1989 | U.S.S.R. | 241/DIG. 38 |

Primary Examiner—Timothy V. Eley
Assistant Examiner—Frances Chin
Attorney, Agent, or Firm—Ned L. Conley

[57] ABSTRACT

Method for decontaminating medical waste by comminuting it and contacting the comminuted waste with an antimicrobial agent.

1 Claim, 2 Drawing Sheets 5,209,411

DECONTAMINATION OF MEDICAL WASTE

This is a continuation of copending application Ser. No. 07/589,185 filed on Sep. 19, 1990 now abandoned.

This invention relates to improvements in decontamination and disposition of medical waste material.

BACKGROUND OF THE INVENTION

In the past few years, federal, state and local governments, the scientific community and the public in general have become acutely aware of the problem of handling of possibly infectious medical waste generated by hospitals and other medical treatment facilities. Because of the concern for possible adverse effects on persons who may come into contact with such waste, various regulatory agencies have acted to control and direct the handling of such waste. In addition, the Congress of the United States has enacted the Medical Waste Tracking Act which is being evaluated in several states. This Act mandates that medical waste be rendered unrecognizable from its original state and be decontaminated or disinfected before disposal.

The transportation and disposal of untreated medical waste presents an expensive and potentially hazardous situation. Moreover, the storage of such waste until such time as it can be properly handled involves serious logistic problems. Some hospitals generate tons of such waste every week and find it extremely difficult and expensive to handle it in such a way as to avoid violation of the Act and, more importantly, to avoid injury to any persons who may come into contact with the waste. In addition, treatments presently available for decontaminating such waste to the extent that it can be transported and disposed of in landfills or other waste disposal facilities have become extremely expensive and difficult.

SUMMARY OF THE INVENTION

According to the present invention, medical waste is passed through a comminuting device, or series of comminuting devices, in which it is comminuted to the extent that the individual elements of the waste are rendered unrecognizable. The comminuted waste is then passed through a decontamination chamber preferably comprising a perforated rotatable vessel which is rotated to agitate and tumble the comminuted waste material while at the same time the waste material is contacted with an antimicrobial agent which passes through the decontamination chamber. After a suitable decontamination period, the decontaminated material is removed from the chamber and passed to storage containers in which it may be transported to a sanitary landfill or other garbage disposal facility.

DETAILED DESCRIPTION OF THE PREFERRED EMBODIMENT

According to this invention, medical waste is first passed through a suitable comminuting device or a series of comminuting devices which comminute the various materials in the waste to such an extent that the individual elements of the waste are not recognizable. As is well known, such medical waste may include syringes, wrappings, tubular materials and a variety of other articles which are disposed of after contact with persons being treated. The comminuting devices used may be of any suitable type for comminuting such a variety of materials. For example, some types of grinders, hammer mills or shredders, such as blade type shredders, may be used for this purpose. It is important that the comminution be to such a size that the particles produced are not only unrecognizable, but that they be torn apart to the extent that all portions may be intimately contacted by an antimicrobial agent.

Following the comminution, the waste material passes to a decontamination chamber in which the waste material is intimately contacted by an antimicrobial agent. The antimicrobial agent is one which is suitable for permanently deactivating bacteria, viruses and other human pathogens. Examples of such antimicrobial agents include hot air, steam, alcohol chemical vapor, ethylene oxide, hydrogen peroxide plasma, gamma radiation, ultraviolet radiation, and combinations of these and other agents.

In order to insure thorough and intimate contacting between all portions of the waste material and the antimicrobial agent, it is desirable that the comminuted waste material be agitated, as for example by means of mechanical agitators, or by propelling the antimicrobial agent at high velocity. Such agitation allows greater exposure of the waste to penetration of the antimicrobial agent thus accelerating the decontamination.

In one embodiment of the invention, the comminuted waste is contacted with the antimicrobial agent in a rotatable perforated vessel of cylindrical cross section, such as circular, octagonal or hexagonal. The vessel may for example be constructed of wire mesh which is suspended within a chamber, the chamber being rotatable around a horizontal axis and driven by a suitable motor and gear drive.

Figure 1:
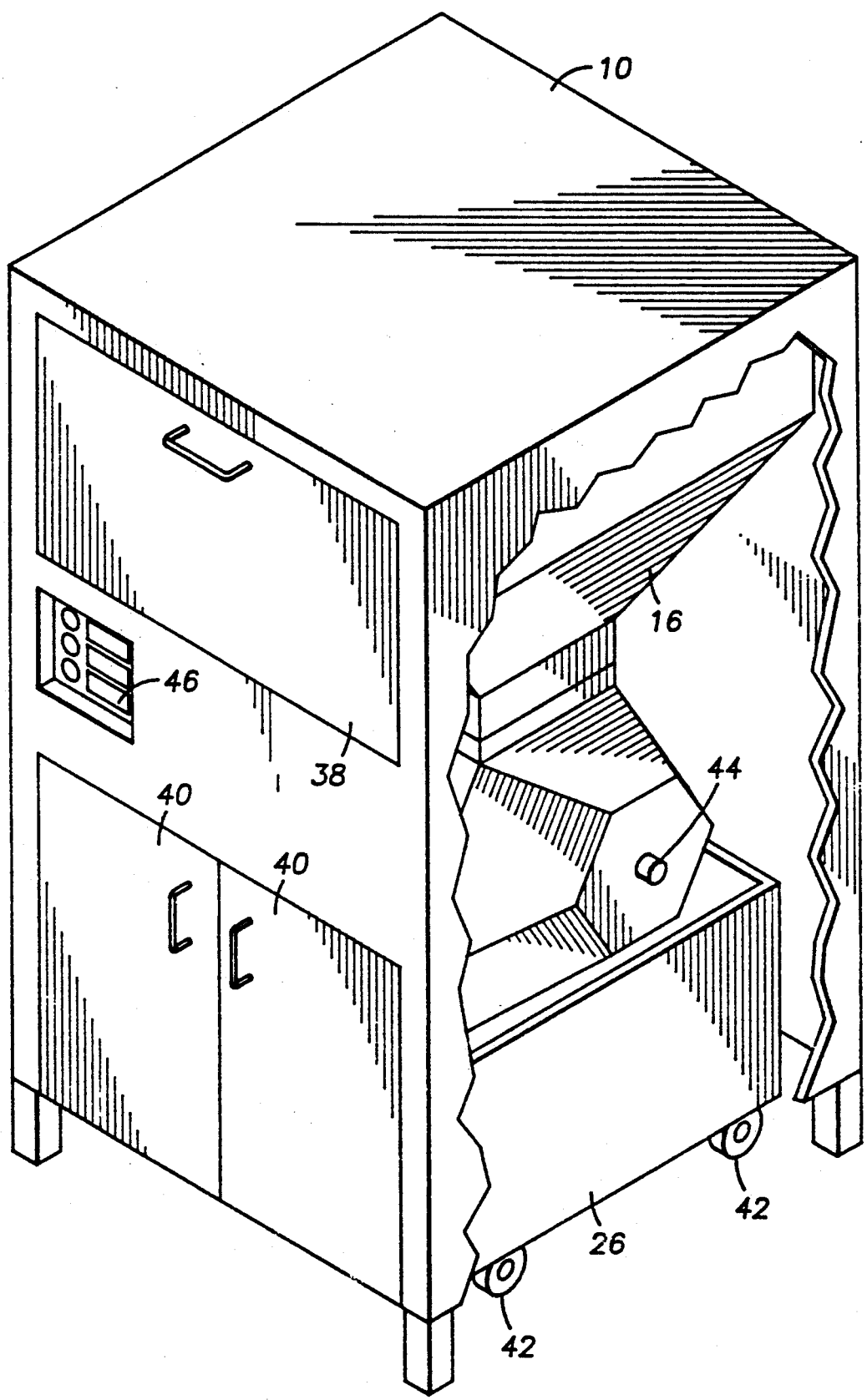
FIG. 1 of the drawing is a perspective view of one embodiment of the apparatus of the present invention.
Figure 2:
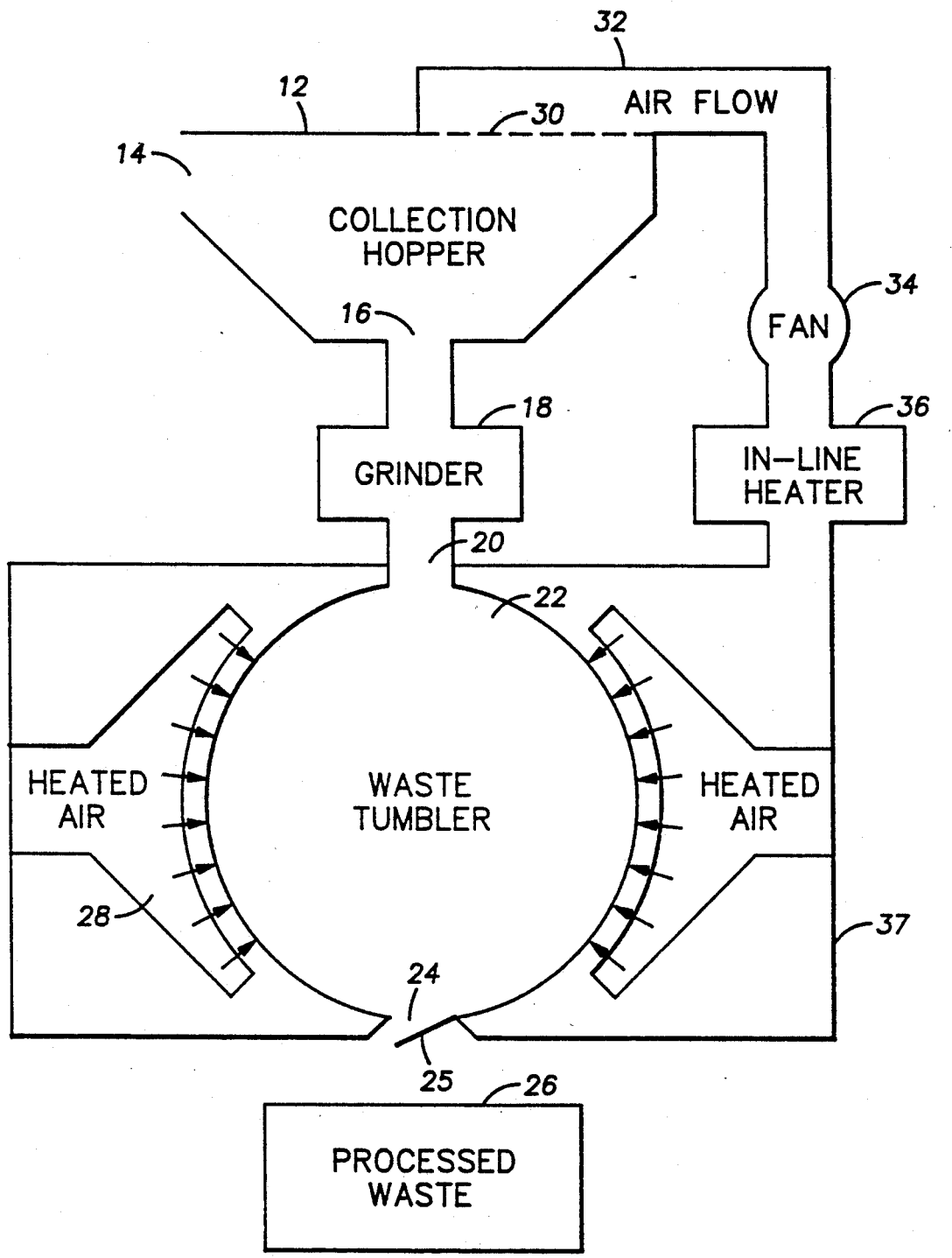
FIG. 2 is a schematic drawing showing one embodiment of the elements of the apparatus of the invention and illustrating the steps of one embodiment of the method of the invention.

The drawing illustrates one form of apparatus which may be used to practice the process of this invention. In this form, the apparatus is designed for use in a hospital or other treatment facility and is enclosed within a cabinet 10, as shown in FIG. 1. As shown in FIG. 2, the cabinet includes a collection hopper 12 having an inlet 14 and an outlet 16. The outlet 16 leads to a grinder 18 which in turn has an outlet 20 to pass the comminuted material to the waste tumbler 22. The waste tumbler 22 has an outlet 24 having a closure 25 to pass decontaminated waste to a container 26. Means are provided at 28 for directing heated air through the waste tumbler. After contacting the waste material, the air passes upwardly through the outlet 20, the grinder 18, and the collection hopper 12 and out the top of the collection hopper through a screen or mesh 30 which restricts the flow of solid materials. The air then passes through a duct 32 and is propelled by a fan or blower 34 and heated by in-line heater 36. The waste tumbler 22 and the heated air distribution 28 may be carried within a chamber 37.

Referring again to FIG. 1 of the drawing, the inlet 14 to the collection hopper is covered by a door 38. Doors 40 may be opened to permit removal of the container 26 of processed waste material which may for example be fitted with wheels 42 for ease of transport. A shaft 44 is shown for connection to a suitable motor drive for the waste tumbler. A switch panel 46 is provided for operating the grinder, the motor and the in-line heater.

In operation, waste material is put into the apparatus by opening the door 38 and depositing directly into the collection hopper. The grinder may be operated immediately to grind each deposit of waste material, or grinding may be delayed until a large amount of waste material has been deposited in the hopper. Preferably safety switches will be provided so that the grinder cannot be operated while the door 38 is opened. When it is desired to decontaminate a batch of material, the in-line heater, the fan and the waste tumbler drive motor are energized and the grinder is then started to comminute the waste material and drop it into the waste tumbler. The material will be tumbled for such period of time as is determined to be sufficient to obtain the desired degree of decontamination, at which time the apparatus will be turned off, the door 24 will be opened and the decontaminated waste material will be deposited in the container 26.

Numerous variations in the apparatus and process described may be made without departing from the invention. For example, if it is desirable to use a pressurized form of antimicrobial agents, the cabinet or other chamber may be pressurized. Apparatus may be included to gage the degree of comminution of the waste material so as to insure that it is subdivided sufficiently for the purposes of the invention. The apparatus may be made for continuous process rather than for batch process. These and other variations which will be apparent to those skilled in the art are incorporated in the invention.

We claim:

1. A method for decontaminating medical waste comprising:
   - comminuting the waste to an extent that substantially all surfaces of the waste are available for contact by an antimicrobial agent,
   - passing a gaseous antimicrobial agent countercurrently to and through the comminuted waste while tumbling the waste sufficient to intimately contact the comminuted waste with the antimicrobial agent,
   - then passing the antimicrobial agent countercurrently to and through the uncomminuted waste,
   - then regenerating the antimicrobial agent, and
   - passing the regenerated antimicrobial agent through comminuted waste.

* * * * *